(12) United States Patent
Christoff

(10) Patent No.: US 9,113,827 B2
(45) Date of Patent: Aug. 25, 2015

(54) INTRAORAL X-RAY IMAGING DEVICE WITH OPTIMIZED IMAGE DATA OUTPUT

(71) Applicant: Jordan C. Christoff, Santa Barbara, CA (US)

(72) Inventor: Jordan C. Christoff, Santa Barbara, CA (US)

( * ) Notice: Subject to any disclaimer, the term of this patent is extended or adjusted under 35 U.S.C. 154(b) by 83 days.

(21) Appl. No.: 13/744,356

(22) Filed: Jan. 17, 2013

(65) Prior Publication Data

US 2014/0198901 A1 Jul. 17, 2014

(51) Int. Cl.
*A61B 6/14* (2006.01)
*A61B 6/00* (2006.01)

(52) U.S. Cl.
CPC ............... *A61B 6/145* (2013.01); *A61B 6/425* (2013.01); *A61B 6/563* (2013.01)

(58) Field of Classification Search
CPC ......... H01J 35/10; H01J 35/101; H01J 35/26; H01J 35/16; A61B 6/145; A61B 6/563; A61B 6/425; G06F 19/321; G06F 19/3406; G06F 19/3418; G06F 19/322; G06F 19/345; G06F 19/3412; G06F 19/3443; G06F 19/3481; G06F 3/00; G06F 3/0484; G06F 3/04842; A61C 9/0006; A61C 13/0004; A61C 19/04
USPC ................................ 378/125, 121, 138, 140
See application file for complete search history.

(56) References Cited

U.S. PATENT DOCUMENTS 8,119,990 B2 * 2/2012 Zeller ..................... 250/370.09
2006/0077143 A1 * 4/2006 Kwon ............................ 345/77

* cited by examiner

*Primary Examiner* — Irakli Kiknadze
(74) *Attorney, Agent, or Firm* — W. Edward Johansen

(57) ABSTRACT

An intraoral x-ray imaging device produces and transfers intraoral images of a patient to a network and which includes intraoral housing, an x-ray image sensor which is disposed in the intraoral housing, a digital high-bit generator which generates digital high bit depth grayscale sensor data and which is disposed inside the intraoral housing, a digital low-bit generator which converts the digital high bit depth grayscale sensor data to low bit depth grayscale sensor data and which is disposed inside the intraoral housing and a communication device which couples the digital low-bit generator to the network.

9 Claims, 14 Drawing Sheets

INTRAORAL X-RAY IMAGING DEVICE WITH OPTIMIZED IMAGE DATA OUTPUT

BACKGROUND OF THE INVENTION

1. Field of the Invention

This invention relates generally to dental imaging systems and more particularly to intra-oral sensor based imaging systems with optimized image data output that obtain, manipulate, process, and electronically store and display dental image data.

2. Description of the Prior Art

X-rays have been used in dentistry to image teeth and parts of the mouth for many years. In general, the process involves generating x-rays outside the patient's oral cavity and directing the x-rays at an image receptor located in the patient's mouth. The x-rays are attenuated differently by different parts of the patient's dental structures (e.g., bone versus tissue) and this difference in attenuation is used to create an image, such as on film or by using an electronic image sensor. In most cases, the x-ray source is triggered manually by the operator. In other words, the capturing of an image is initiated by a technician or other person by, for example, activating a switch. In the case of film-based systems, the image is captured as soon as the film is exposed to x-ray radiation. So, there is no need to "activate" the film. Once the x-ray source is activated and the x-rays reach the film, an image is captured. In electronic systems, the particular image captured depends on at least two factors: activation of the x-ray source and "activation" of the sensor. What constitutes "activation" of the sensor can vary based upon the type of sensor used, but in most cases "activation" occurs when a command is provided to the sensor to either store or output its current image data (referred to herein as "image capture"). In some systems, there is an electrical link between the x-ray source and the sensor such that when the x-ray source is activated, a command is sent (simultaneously or nearly simultaneously) to the sensor to perform an image capture. In other systems no physical link is established between the x-ray source and sensor. In these systems the activation is initiated via alternate means such as comparing to a reference threshold or via a photo sensor to detect the source. Thus, whether the x-ray source is wired to the sensor or not, it is possible to generate a burst of x-ray radiation and be assured that an image will be captured by the sensor during the relatively short period of x-ray exposure.

Digital intraoral radiography x-ray imaging via sensors has become increasingly popular over the past 15+ years. Digital x-ray sensors capture and display near instant x-ray images of the patients dentition including jaw, tissue and teeth and are used for dental diagnosis and treatment. More than 50+ percent of USA dentists have replaced traditional intraoral film and employ some form of digital intraoral radiography imaging in their practices.

A digital intraoral sensor is used on a patient via inserting sensor inside the oral cavity and then exposing the sensor to radiation from an x-ray source that is located outside the oral cavity, which is exactly the same technique as exposing intraoral film.

Traditional digital intraoral x-ray sensors contain a CCD, CMOS, or other type of imager and a means for converting X-rays into visible light, most commonly via a scintillator and optional fiber optic plate. There are also direct x-ray conversion techniques to convert x-ray photons directly to electrons without a traditional scintillator, such as Cadmium Telluride but for intraoral radiography these have not been mass produced as of 2012. The imager, scintillator; if so equipped, and optional fiber optic assembly is then encased in a water resistant plastic or metal housing and a cable is attached to route the electrical and data signals from the sensor to outside of the oral cavity.

An additional piece of electronics commonly referred to as a "controller" is connected to the other end of the sensors cable and generates the necessary power and electronic signals required to operate the sensor, and also contains the analog to digital convertor which digitizes the analog output of sensor to digital high bit grayscale (12-16 bit or higher grayscale) image data.

Referring to FIG. 1 an intraoral x-ray sensor has a controller attached. The controller also contains the required circuitry to deliver the high bit depth grayscale image data to a computer, be it via a pci, usb, wireless, or other type of connection. Once the high bit grayscale sensor image data is transferred to the host PC computer via the controller, the data is processed by application software on the host PC and transformed into a "presentable dental x-ray image" that is displayable on a typical PC. This processing of the high bit depth data usually includes 2 point correction, noise removal, bad pixel correction, sharpening, blurring, or convolution operations and always includes a conversion from 12-16 bit grayscale data in some form (linear or nonlinear) to an 8 bit grayscale image that is ultimately displayed on the Dentist's monitor that is only capable of displaying 8 bit grayscale data.

U.S. Pat. No. 7,959,355 teaches an apparatus which includes an intraoral dental X-ray electronic sensor facing an x-ray source and connected to a signal processing unit that allows taking and storing multiple x-ray images even without the unit to be connected to database computer. The processing unit has a memory that may be equipped with energy source and the unit is mounted on the sensor holder and can be easily removed from it. The images from the memory can be downloaded into a database using standard serial digital interfaces during or after the image acquisition.

Providing advanced dental services require continuous improvement in the quality and convenience of the dental procedures. This invention offers a method and apparatus for dental imaging that provides ultimate simplicity, easy operation and patient comfort in taking full mouth dental x-ray series (FMS), further referred only as image series. The process of taking FMS includes composing up to 18 images four bitewings, eight posterior periapicals and six anterior periapicals.

Referring to FIG. 2 a digital dental intraoral system includes an intraoral x-ray sensor a signal processing unit, a power source and a unit holder. The processing unit shows multiple openings for light emitting diodes (LED) and a button.

Referring to FIG. 3 the main functional blocks of the sensor system includes the digital x-ray sensor, signal processing unit, power source unit (3). The processing unit incorporates analog front end, sensor timing circuit (STC), controller, memory (interface circuit and power management. The power source unit may consist of energy source (battery), power management, interface circuit, memory, communication device and micro-controller. The microcontroller manages the image acquisition process. The image is acquired when appropriate timing controls (clocks) are applied to the sensor and the analog frontend converts the analog sensor output to digital pixel values then those values are properly recorded in the memory. Some components from the signal processing unit are duplicated into the battery unit in order to support the image interface between the signal processing unit and the storage database. The controller is a device that manages the acquired data and synchronizes the readout process. The memory is present to store or help transfer the images from the sensor to the storage device. The interface circuit implements the actual interface of transferring the image to the file storage device. The power management delivers the power necessary for the operation of the system. The energy source provides the electrical power necessary for the image acquisition process. The communication device allows wireless interface connection when the unit is operating. The microcontroller can provide indication as example a display for the image after the acquisition. The display can be displaying number of characters, illuminated light, like example light indication from light emitting diode (LED), with certain color or pattern or any similar visual or sound related feedback.

U.S. Pat. No. 7,010,089 teaches an apparatus which includes but not limited to a charge-coupled device (CCD-array sensor positioning mechanism, the positioning mechanism structured to position a CCD-array sensor to capture a first target area; and the CCD-array sensor positioning mechanism further structured to position the CCD-array sensor to capture a second target area proximate to the first target area, the first and second target areas spatially related such that a first radiographic image recorded at the first target area may be combined with a second radiographic image recorded at the second target area to form a composite radiographic image substantially analogous to a single radiographic image of an aggregate target area covered by the first and second target areas.

Non-CDR dental imaging systems traditionally use radiographic film to obtain and capture dental images. Non-CDR dental imaging systems can capture a number of traditional "views" of a patient's teeth and associated bony structures. Three such traditional views upon which dental professionals heavily rely are the bitewing, periapical, and occlusal views.

Unlike non-CDR systems, CDR systems utilize charge-coupled device (CCD) array sensors, rather than radiographic film, to directly obtain digital dental images. Since CDR systems allow the dental images to be captured directly to digital form, such CDR systems affect the "paperless" dental office, in that the images are stored in digital format (e.g., on CD-ROM or magnetic disk drive) rather than film. Readily available commercial embodiments of such CDR systems may be obtained from several companies, such as Schick Technologies, of Long Island, N.Y.; Trophy Radiology Inc., of Marietta, Ga.; Dexis Dental, of Palo Alto, Calif.; and Dentsply International Inc.'s Gendex Division, of Des Plaines, Ill.

CDR systems have many advantages. Examples of such advantages are that CDR systems do not require radiographic film, nor do they require the processing capabilities and darkroom capabilities necessary to develop the radiographic film into a traditional radiograph, nor do they require traditional backlit radiographic viewers. However, CDR systems are not without disadvantages.

Significant disadvantages associated with CDR systems are associated with the extremely high financial and or technical costs associated with the engineering and production of the CDR-system CCD-array sensors. Those having ordinary skill in the art will recognize that while standard digital cameras use CCD-array sensors, and the cost of such CCD-array sensors is beginning to come down with mass production, the financial and or technical costs associated with engineering and producing CDR-system CCD-array sensors are now, and are expected to remain in the future, extremely high. One reason for such high financial and technical costs is that CDR system CCD-array sensors require much, much greater pixel resolution than standard digital camera CODs. Non-CDR radiographic film has resolution of about 14 lines per millimeter. Insofar as CDR system digital images are intended to replace the non-CDR radiographic film images, every effort is made in the industry to produce CDR-system CCD-array sensors capable of capturing a digital image having resolution comparable to the non-CDR system radiographic film.

At present even though the industry has expended considerable financial and technical resources, the average resolution available with CDR-system CCD-array sensors is about 8 lines per millimeter; thus, currently available CDR-system CCD-array sensors tend to be very expensive due to expenditures associated with past efforts to achieve the resolution of the radiographic film and continuing efforts to continue to approach the resolution of the radiographic film.

Another reason for the high financial and technical costs associated with CDR-system CCD-array sensors is that CDR system CCD-array sensors require much, much greater grayscale resolution than standard digital camera CODs (each CCD-array sensor pixel has a value, proportional to the amount of absorbed radiation, which is converted to a grey level). Non-CDR radiographic film, being an extremely sensitive analog recording device, tends to reproduce gray scale shading with extremely high resolution. In contrast, CCD-array sensors, being digital recording devices, must produce the gray scale in steps (e.g., 0 264 "shades" of gray), and producing CCD-array sensors capable or such gray scale resolution also tends to be very financially and/or technically expensive, for reasons similar to those associated with the high pixel resolution requirement. Yet another reason for the high financial and technical costs associated with CDR-system CCD-array sensors is that CDR-system CCD-array sensors detect X-ray frequency photons, and since the energy per photon in X-rays is substantially greater than the energy per photon of visible light, the CDR-system CCD-array sensors must be able to withstand significantly more wear and tear than the CCD-array sensors used in the standard digital camera; thus, engineering and producing such rugged CCD-array sensors also tends to be relatively expensive financially and/or technically.

A consequence of the foregoing-described cost issues related to CCD arrays utilized in the CDR systems is that CDR systems do not, in general, provide readily available digital images of occlusal views because of the financial cost and technical difficulties associated with constructing CCD-array sensors of a size necessary to capture the views. The target area of occlusal views tends to be, on average, roughly four times (4.times.) the target area of CDR-system CCD-array sensors currently available. Because of the foregoing-noted technical issues associated with CDR-system CCD-array sensors, increasing the size of a CCD necessary to capture an image within a larger target is not a linear operation in either financial cost or technical difficulty. Rather, doubling the size of the target area to be captured by a CDR-system CCD-array sensor could have an associated cost/technical difficulty logarithmically proportional to that associated with the smaller target area, while quadrupling the target area could have an associated cost/technical difficulty logarithmically proportional to that associated with the smaller target area.

Accordingly, due to financial and/or technical difficulty issues, CDR systems do not generally provide digital images of occlusal views, since the target area of such occlusal views tends to be, on average, roughly four times the target area of CDR system CCD-array sensors currently available. Irrespective of the foregoing-noted difficulties, as noted above, dental professionals have a longstanding and ongoing reliance on occlusal view radiographic images.

Over the last 5+ years two newer more integrated and/or expanded features have emerged. The first feature is that sensors have more integrated electronics. The sensor controller that is on existing sensors is an external enclosure of electronics attached to the end of the sensor cable and is now embedded directly inside the housing of the sensor, either in the CMOS imager die or as discrete components attached inside the sensor housing or via a very small "stick of gum" sized external controller attached into the middle of a USB terminated cable. This eliminates the additional external controller that previous systems required.

Referring to FIG. 4 a Dexis Platinum sensor has integrated controller/USB electronics.

Referring to FIG. 5 a Kodak RVG6000 has a very small controller integrated into the middle of the cable.

Referring to FIG. 6 a second type of recent improvements to digital x-ray sensors is related to a true wireless sensor (Schick) or sensors with wireless data transfer capabilities (Schick and Kodak) which are called tethered wireless sensors. These sensors are more mobile, have no and/or shorter cables and transmit the high bit depth sensor data wirelessly to a host computer for processing/display.

Referring to FIG. 7 in conjunction with FIG. 8 recently Schick and Kodak have introduced "tethered wireless" sensors that have a short cable exiting the sensor housing/oral cavity and are attached to portable battery powered controllers with wireless high bit depth image data transmission to a host PC for processing and display. Schick also previously introduced a battery powered wireless self contained sensor that can be placed in the mouth and has no cable attached. This product has proved to not work well and could not transmit the data reliably out of the patient's oral cavity because of fillings and various other obstacles. The Schick and Kodak tethered wireless sensors shown in FIG. 7 and FIG. 8 allow greater mobility and improved cable management as compared to traditional wired sensor systems.

U.S. Pat. No. 5,514,873 teaches an x-ray apparatus which has a portable radiation detector having a housing containing a radiation transducer formed of individual detector cells that convert incident radiation, particularly x-radiation, into electrical signals. The radiation detector is implemented cable-free. A wireless transceiver for the in-feed of operating energy and for the outfeed of the signals is provided. An advantage of this radiation detector is the cable-free construction, and the simple manipulation and reusability resulting there-from. Moreover, the radiation detector is better suited to hygienic demands. The filmless dental radiography system attempts to solve the problem of the cable. A radiation detector is inserted into the mouth of the patient in a manner similar to the manner in which conventional x-ray film is exposed. Images are captured by converting incident x-radiation to electrical signals, which electrical signals in turn are conducted via the control logic to an electromechanical coupling element. After the image is captured, the detector is removed from the patient's mouth and physically coupled to an evaluation unit via the electromechanical coupling element. The signals from the detector are sent to the evaluation unit via the electromechanical coupling element, and the evaluation unit processes the signal into an image.

After the signals have been read out of the detector in this fashion, the detector is reset to prepare it for the next exposure. The detector is uncoupled from the evaluation unit and re-inserted into the next position in the patient's mouth.

While this arrangement operates without using a cable to connect the sensor, the radiation detector must be removed from the mouth and inserted into the evaluation unit after each image is captured.

Thus, for a standard set of eighteen x-rays, the process of positioning the radiation detector in the patient's mouth; exposing the detector; removing it from the patient's mouth; and inserting it into the evaluation unit must be repeated eighteen times. This approach is plainly cumbersome, and in fact is less desirable than a system that uses a cable, since in a cable system images are obtained instantly without removing the sensor from the patient's mouth, and the sensor can be moved directly from one position in the mouth to the next. A sensor may use a wireless transceiver in place of the electromechanical coupling element and adds a memory. The memory stores multiple images, so that the radiation detector need not be removed from the mouth and inserted into the evaluation unit between each exposure. Instead, the radiation detector can be moved directly from one position to the next position inside the mouth until all the desired images are captured. The communication from the wireless transceiver to the evaluation unit is inductive, capacitive or electro-optical.

Accordingly, once all the images have been captured, the radiation detector must still be removed from the mouth and placed in close proximity to the evaluation unit so that the stored signals can be read out.

Even with this approach, however, there are a number of disadvantages. First of all, because the radiation detector must be removed from the mouth to be read out, instantaneous images still cannot be obtained. Thus, this approach shares a disadvantage with traditional film-based x-rays: images cannot be viewed until all the images are collected and subsequently transmitted into the console. As a result, there is no way to know when a given image is defective until after the radiation detector is removed from the patient's mouth. Moreover, the detector is necessarily more complex because significant memory must be provided, along with a control system capable of recognizing exactly when a given image is to be captured and stored. This second approach, therefore, is again less desirable than cable-based systems.

U.S. Pat. No. 5,434,418 teaches an intra-oral sensor which is for computer aided oral examination by means of low dosage x-rays in place of film and developer. The intra-oral sensor is exceedingly thin for proper mouth placement and in situ maneuvering, with an active area substantially equivalent to corresponding dental film sizes and a thickness of no more than about 3 mm. In addition, the sensor contains limited electronics and no optical elements, and is resistant to moisture and heat and is readily autoclaved. The sensor consists of a thin, large area semiconductor image array such as a modified charge coupled device (CCD) or photodiode array, coated with a thin, epitaxial growth of a material such as thallium doped cesium iodide CsI(Tl). The coated sensor is bonded to and supported on a passivated ceramic chip, and has an integrated signal amplifier, with the entire assembly being coated with a protective inert plastic layer, e.g., polytetrafluoroethylene, which is pervious to x-ray radiation. The CsI(Tl) is sensitive to x-ray photons, efficiently converting them into visible photons in the 500-600 micron range. To reduce light spreading within the CsI(Tl) layer, growth of the CsI(Tl) layer is directed into narrow (20 microns) columns. Visible photons are detected by the large area semiconductor array and the output is monitored by a computer until polling of the CCD or photodiode array indicates that there is no further conducting. A signal thereafter causes a read out of the electrical charges for translation from analog to digital signals of images with computer display and analysis.

Both of the above designs allow these sensors to have a cable that terminates with a USB connector attached and can be directly plugged into a computer with a USB port. This is in improvement over original sensor designs and minimizes or eliminates, from a user's perspective, the bulky controller and the additional cable connection required in traditional designs to send sensor data to the PC.

U.S. Pat. No. 7,193,219 teaches an intraoral sensor which includes a radiation sensitive sensor array, an event detection circuit and a transmitter. The radiation sensitive sensor array includes a scintillator which converts x-rays into visible light radiation, and a plurality of pixels sensitive to visible light radiation to capture an image upon the presence of incident radiation. The event detection circuit includes a current sensing device and is configured to generate a triggering signal indicating the presence of radiation incident on the sensor array based upon the amount of electrical current drawn by the sensor array. The transmitter is adapted to transmit via a wireless link signals representing an image captured by the sensor array.

Dentists and oral surgeons typically use x radiation to obtain images of their patient's teeth, mouths and gums to aid in diagnosis and treatment. In traditional oral and dental radiography, a cartridge containing photographic film is placed in the patient's mouth, for example behind a patient's tooth, and an x-ray beam is projected through the tooth and onto the film. The film, after being exposed in this manner, is developed in a dark room or a closed processor using special chemicals to obtain a photographic image of the tooth. More recently, the field of filmless dental radiography has emerged. In filmless dental radiography, an x-ray beam is still projected through the patient's tooth, but no photographic film is used. Instead, an electronic sensor is placed in the patient's mouth behind the tooth to be examined. The electronic sensor may include a charge-coupled device (CCD), a complementary metal-oxide semiconductor (CMOS) active pixel sensor (APS) array or any other filmless radiation sensor. The x-rays pass through the tooth and impinge on the electronic sensor, which converts the x-rays into an electrical signal. The electrical signal is transmitted to a computer, either directly or through a module containing intermediate processing circuitry. The computer then processes the signal to produce an image on an associated output device, such as a monitor or a printer. Filmless dental radiography offers several advantages over traditional film-based radiography. Most importantly, the electronic sensor is much more sensitive to x-rays than is film, allowing the dosage of x-rays to the patient to be lowered by as much as 90%. Also, the image of the tooth is generated by the computer almost instantaneously, thus eliminating the entire development process, including the use of potentially harmful chemicals. In addition, because the images are generated electronically, they can be stored electronically in a computer database.

Filmless dental radiography systems typically utilize a cable to connect the intraoral sensor to the computer or processing module. Such a cable, however, can be uncomfortable for and annoying to the patient in whose mouth the intraoral sensor is placed. The cable is also bothersome to the dental practitioner when positioning the sensor in the patient's mouth. It would be advantageous to both patient and practitioner, therefore, if the cable connecting the intraoral sensor to the computer or processing module could be eliminated.

U.S. Pat. No. 5,454,022 teaches an intraoral sensor which includes a CCD, CCD control and processing circuits, a battery, an analog-to digital converter (ADC) and a transmitter. A base image system includes a receiver, a display and a power supply connector. The sensor must be re-connected to the base station following each exposure. The sensor must be maintained in the record mode for a previously set predetermined period of time while the image sensor is physically and electrically isolated from the base station. Timing each exam like this would be quite cumbersome for the dentist. It would be more desirable to have an efficient mechanism for automatically triggering image acquisition.

There is a need for a filmless dental radiography system that eliminates the cable between the sensor and the computer, and overcomes the obstacles that plague the systems in the prior art.

Referring to FIG. 9 the system includes an intraoral sensor, a base station that includes a radio frequency (RF) receiver and data output ports (not shown), and a host computer. The sensor 1 is placed in the patient's oral cavity, and communicates with the RF receiver of the base station 2, which is located outside the oral cavity, via wireless RF link, as will be discussed in greater detail below. The base station communicates with the host computer over a bi-directional wired link 5. Preferably, the communication between the base station 2 and host computer 3 is via the widely available and accessible Universal Serial Bus port, as described in U.S. Pat. No. 6,134,298. The base station may also communicate with the host computer via the computer's Peripheral Component Interconnect (PCI) bus, a high-speed Firewire bus, or via the computer's Industry Standard Architecture (ISA) bus. In such a case, a special purpose board normally would be housed in the host computer to facilitate such communication. In any case, the communication between the sensor and host computer 3 should be direct and nearly instantaneous. The host computer may be any conventional desktop, tower, laptop or notebook computer, equipped with software for processing the data provided to it. The computer is either connected to or has built in one or more input devices, such as a keyboard 6 or a mouse, and one or more output devices, such as a monitor or a printer. These devices allow the user to control the operation of the system, and to view the dental images that the system creates. The computer might also include or be connected to some type of storage device (not shown), such as a hard drive, for permanent storage of the images in patient files.

Referring to FIG. 10 the sensor is divided into four subsystems: a Sensor Subsystem (SSS) that includes the actual sensor array, an event detection module, a single-pole double-throw analog switch and a biasing voltages module 213; a Data Processing Subsystem (DPSS) that includes a complex programmable logic device (CPLD)(which among other things provides clock signals CLK to the sensor array, light emitting diodes (LEDs), a analog-to-digital converter (ADC), a radio frequency (RF) module, a 10 MHz clock oscillator and operational amplifiers (op amps); a Core Subsystem (CSS) that includes a microcontroller; and a Power Supply Subsystem (PSS) that includes a power source (such as for example a replaceable battery) and other components that will be described below. The organization of the sensor electronics into subsystems facilitates the implementation of a novel power management technique, as will be explained in greater detail below. The power source provides all necessary power to the sensor array and the other various electronic components of the sensor. In accordance with the present invention, the sensor is configured such that it is capable of transmitting image data to the base station from within a patient's mouth, and is further configured such that it is capable of transmitting to the base station image data representing multiple intraoral images without requiring that it be removed from the patient's mouth for power source or replacement. Preferably, the sensor of the present invention is capable of capturing and transmitting images representing at least a full-mouth series of x-rays (typically 18 images) without requiring that the power source be replaced. To achieve this goal, power consumption of the sensor must be managed carefully and efficiently, to ensure that the limited-life power source on board the sensor 1 can provide power sufficient for the capturing and transmission of the requisite number of images. All components are encapsulated in a hermetically sealed housing so as to be suitable for insertion into the human mouth. The sensor housing is opaque to visible light but radiolucent, i.e. pervious to x-rays. Preferably, the sensor is impervious to liquid penetration and resistant to mechanical damage as could occur if a patient bit on the device or if the device were dropped from standing height. The package is typically scant on available space since the sensor is preferably less than 6 mm thick. The various components must therefore be selected with an eye towards miniaturization. In a preferred embodiment, light emitting diodes (LEDs) on the surface of the sensor packaging comprise a portion of DPSS 22, and are used to indicate status. The sensor body is manufactured from a material such as plastic, to allow carrier waves to be transmitted without interference. The sensor array includes a CMOS APS array, such as for example a CMOS APS array of the type described in U.S. Pat. No. 5,471,515 and U.S. Pat. No. 6,134,298. Each pixel in the APS array includes one or more active transistors which perform gain or buffering functions. The sensor array 210 may alternatively be a CCD, or some other type of solid state device capable of converting electromagnetic radiation into electrical signals. As used herein, the term radiation broadly encompasses all waves in the electromagnetic spectrum. In any case, the sensor array 210 may additionally comprise on top of the CMOS APS array, CCD or other solid state device, a scintillator layer which converts x-rays into visible light, and might further include disposed beneath the scintillator layer a fiber optic faceplate. The remaining components of the sensor, including the remaining electronics of SSS and the electronics of DPSS, CSS and PSS, comprises all of the circuitry necessary to control the exposure and readout of an image, and to provide and manage the requisite electrical power. The specifics of such electronics will vary with the nature of the sensor array 210. These electronics perform the functions of row driver circuitry, reset driven circuitry, column signal chain circuitry, column shift register circuitry and timing and control circuitry, among other things. The SSS includes a novel event detection module that determines when radiation is incident on the sensor array by monitoring the amount of electrical current drawn by the pixels of the sensor array. This novel technique is extremely advantageous, in that it provides a reliable mechanism for detecting the presence at radiation that consumes very little excess power, particularly in comparison with conventional techniques, such as those that use dedicated event-detection diodes. The technique of the present invention is based upon the observation that, in a CMOS imaging array or a CCD imaging array, the magnitude of current drawn by each pixel is itself sensitive to the presence of radiation on the pixel, such that the pixels draw much more current when exposed to radiation and much less when not exposed to radiation. In an APS array, this current is the photo-induced current which flows through each diode in the array. In a CCD, there is a similar phenomenon at the substrate bias or similar point. In either case, the amount of current drawn may be used as a means of event detection.

Dentists and oral surgeons typically use x radiation to obtain images of their patient's teeth, mouths and gums to aid in diagnosis and treatment. In traditional oral and dental radiography, a cartridge containing photographic film is placed in the patient's mouth, for example behind a patient's tooth, and an x-ray beam is projected through the tooth and onto the film. The film, after being exposed in this manner, is developed in a dark room or a closed processor using special chemicals to obtain a photographic image of the tooth. More recently, the field of filmless dental radiography has emerged. In filmless dental radiography, an x-ray beam is still projected through the patient's tooth, but no photographic film is used. Instead, an electronic sensor is placed in the patient's mouth behind the tooth to be examined. The electronic sensor may include a charge-coupled device (CCD), a complementary metal-oxide semiconductor (CMOS) active pixel sensor (APS) array or any other filmless radiation sensor. The x-rays pass through the tooth and impinge on the electronic sensor, which converts the x-rays into an electrical signal. The electrical signal is transmitted to a computer, either directly or through a module containing intermediate processing circuitry. The computer then processes the signal to produce an image on an associated output device, such as a monitor or a printer.

Filmless dental radiography offers several advantages over traditional film-based radiography. Most importantly, the electronic sensor is much more sensitive to x-rays than is film, allowing the dosage of x-rays to the patient to be lowered by as much as 90%. Also, the image of the tooth is generated by the computer almost instantaneously, thus eliminating the entire development process, including the use of potentially harmful chemicals. In addition, because the images are generated electronically, they can be stored electronically in a computer database.

Filmless dental radiography systems typically utilize a cable to connect the intraoral sensor to the computer or processing module. Such a cable, however, can be uncomfortable for and annoying to the patient in whose mouth the intraoral sensor is placed. The cable is also bothersome to the dental practitioner when positioning the sensor in the patient's mouth. It would be advantageous to both patient and practitioner, therefore, if the cable connecting the intraoral sensor to the computer or processing module could be eliminated.

Another wireless system is described in U.S. Pat. No. 5,454,022 an intraoral sensor includes a CCD, CCD control and processing circuits, a battery, an analog-to digital converter (ADC) and a transmitter; and a base image system includes a receiver, a display and a power supply connector. In this invention, the sensor must be re-connected to the base station following each exposure. A second limitation is that the sensor must be maintained in the record mode for a previously set predetermined period of time while the image sensor is physically and electrically isolated from the base station. Timing each exam like this would be quite cumbersome for the dentist. It would be more desirable to have an efficient mechanism for automatically triggering image acquisition. There is a need, therefore, for a filmless dental radiography system that eliminates the cable between the sensor and the computer and overcomes the obstacles that plague the prior art systems.

U.S. Pat. No. 8,119,990 teaches an x-ray sensor. Referring to FIG. 11 in conjunction with FIG. 12 a source emits x-ray radiation towards an x-ray sensor, and the x-ray sensor automatically detects the x-ray radiation. The x-ray sensor automatically detects x-ray radiation by evaluating a time series and determining that a voltage threshold is crossed a certain amount of time earlier than the average time it takes the voltage threshold to be crossed from dark current and other noise.

There is a need, therefore, for a filmless dental radiography system that eliminates the cable between the sensor and the computer, and overcomes the obstacles that plague the systems in the prior art. All existing intraoral x-ray sensors have limitations.

The inventor hereby incorporates all of the above referenced patents into this specification.

SUMMARY OF THE INVENTION

The present invention is generally directed to an intraoral x-ray imaging device which produces intraoral images of a patient and which is coupled to a network. The intraoral x-ray imaging device includes intraoral housing and an image sensor positioned in the intraoral housing.

In a first aspect of the present invention there is a mechanism for converting X-rays into visible light contained either inside or attached to the intraoral housing of the intraoral imaging device.

In a second aspect of the present invention there is a digital high-bit generator which generates digital high bit depth grayscale sensor data.

In a third aspect of the present invention there is mechanism which is coupled to the digital high-bit generator in order to generate digital low-bit depth grayscale sensor data.

In a fourth aspect of the present invention the digital low bit depth grayscale sensor data attaches the intraoral x-ray sensor either directly or indirectly to a non-display device which converts the high bit depth grayscale data to low bit depth grayscale image data.

In a fifth aspect of the present invention there is a communication device which transfers images to a display device.

Other aspects and many of the attendant advantages will be more readily appreciated as the same becomes better understood by reference to the following detailed description and considered in connection with the accompanying drawing in which like reference symbols designate like parts throughout the figures.

The features of the present invention which are believed to be novel are set forth with particularity in the appended claims.

DESCRIPTION OF THE PREFERRED EMBODIMENT

Figure 1:
FIG. 1 is a photograph of a wired intraoral sensor made by Dexis.
Figure 8:
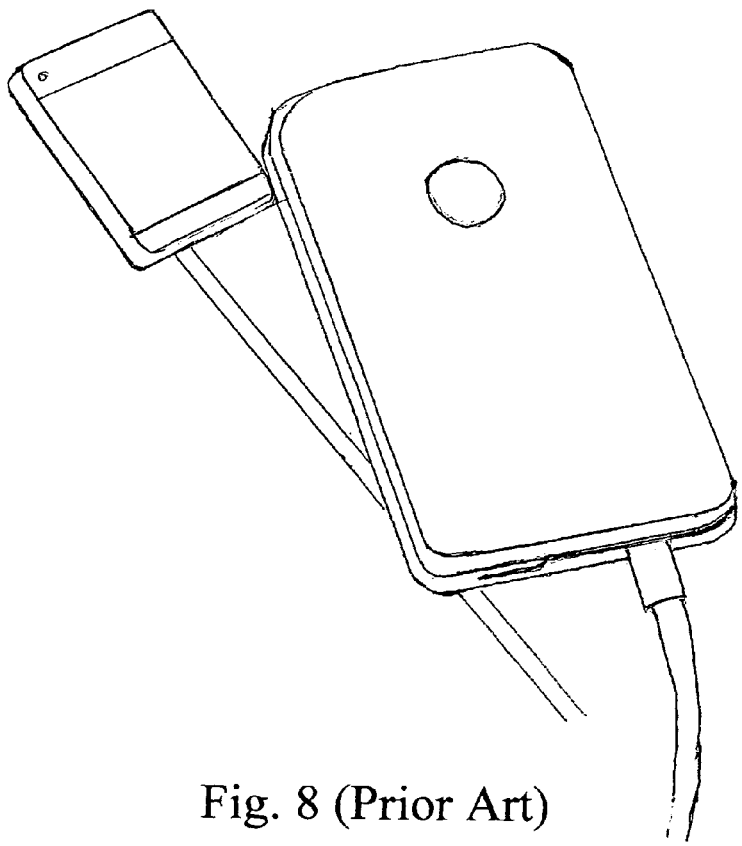
FIG. 8 is a photograph of a tethered wireless intraoral sensor made by Kodak.
Figure 2:
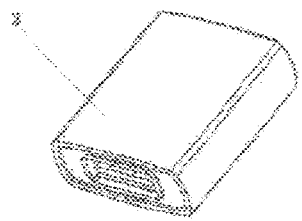
FIG. 2 is an exploded perspective view of an intraoral x-ray system of U.S. Pat. No. 7,959,355.
Figure 2:
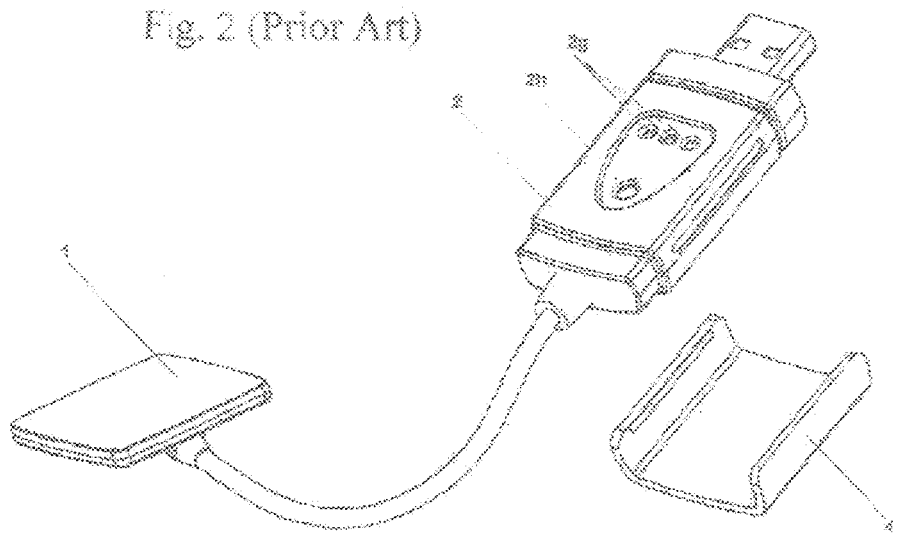
Figure 3:
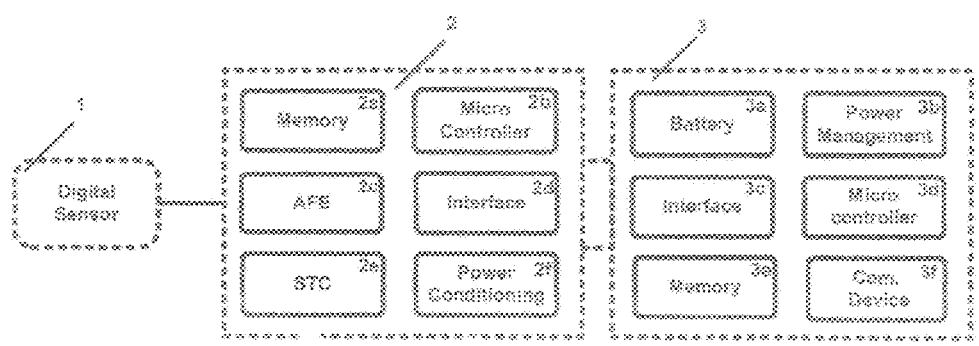
FIG. 3 is a schematic block diagram of the intraoral x-ray system of FIG. 2.
Figure 4:
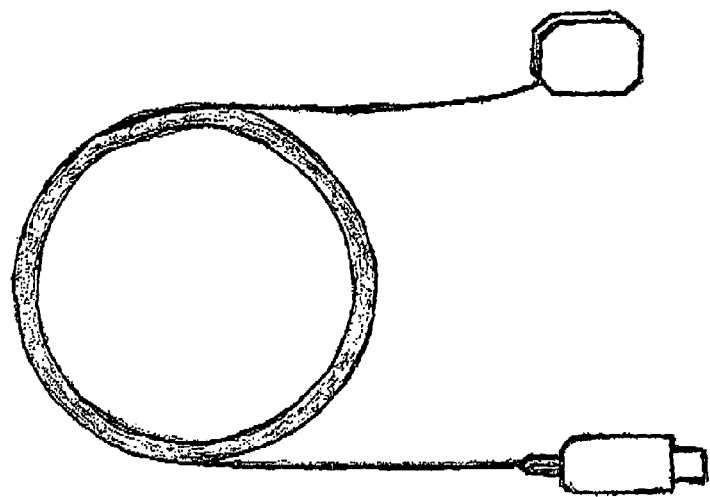
FIG. 4 is a photograph of a wired intraoral sensor made by Dexis.
Figure 5:
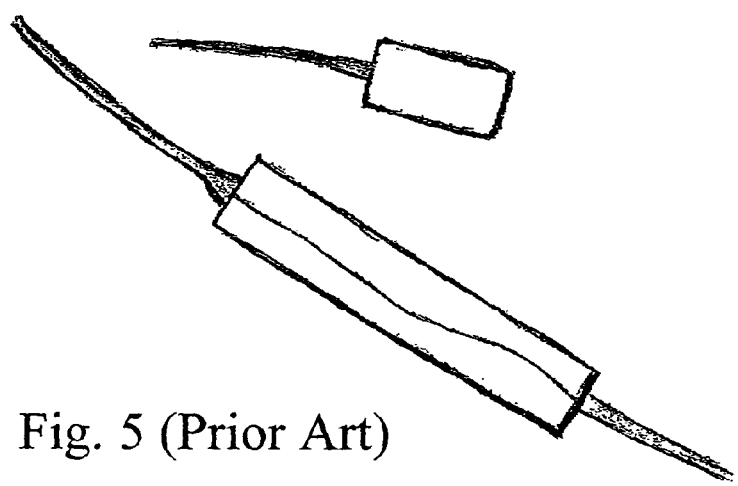
FIG. 5 is a photograph of a wired intraoral sensor made by Kodak.
Figure 6:
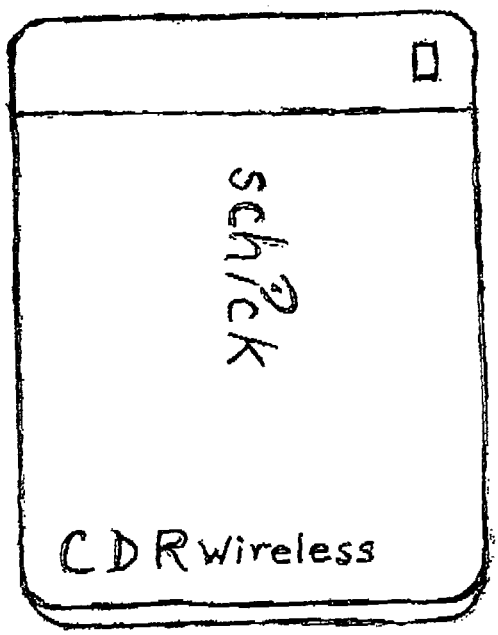
FIG. 6 is a photograph of a wireless intraoral sensor made by Schick.
Figure 7:
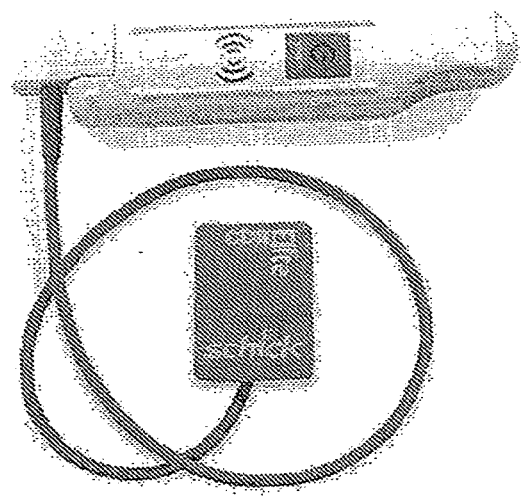
FIG. 7 is a photograph of a tethered wireless intraoral sensor made by Schick.
Figure 9:
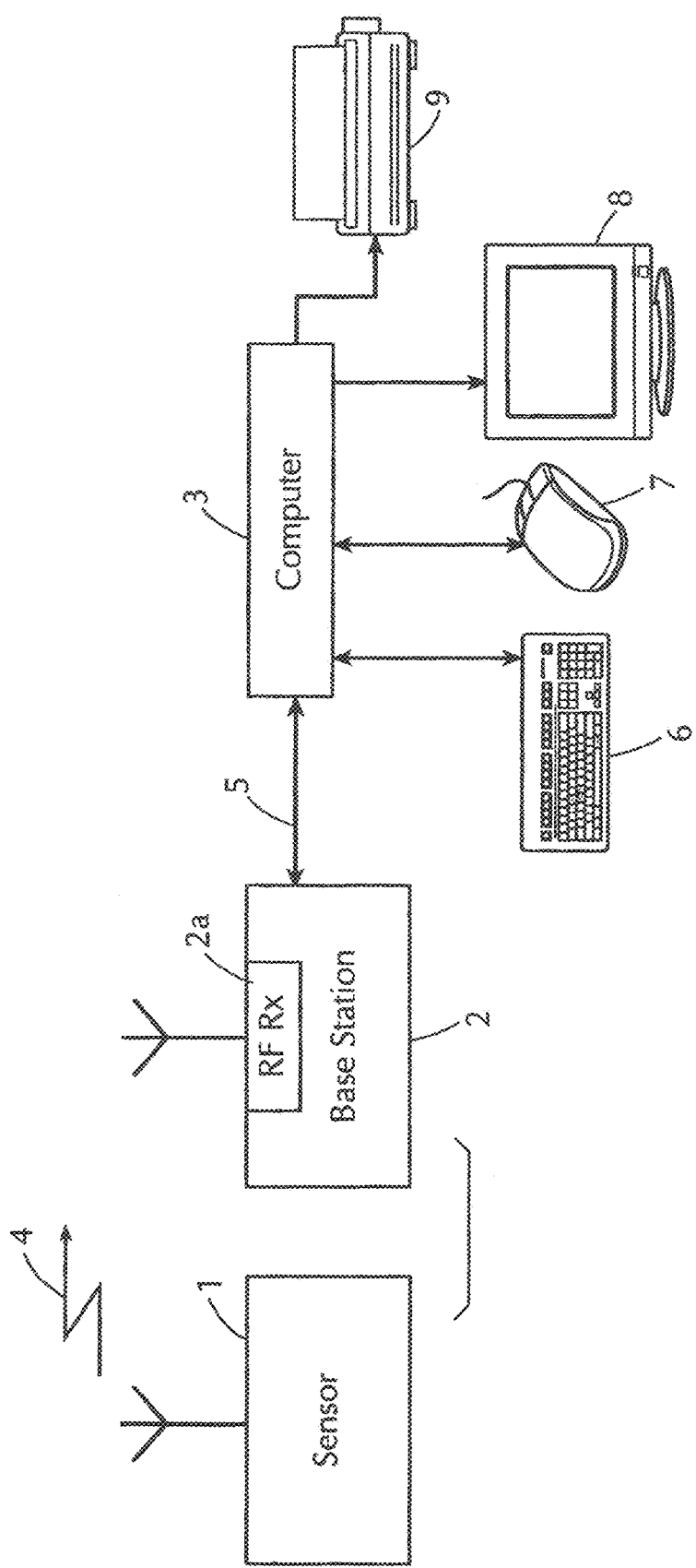
FIG. 9 is a schematic block diagram of a first intraoral x-ray system of U.S. Pat. No. 7,193,219.
Figure 10:
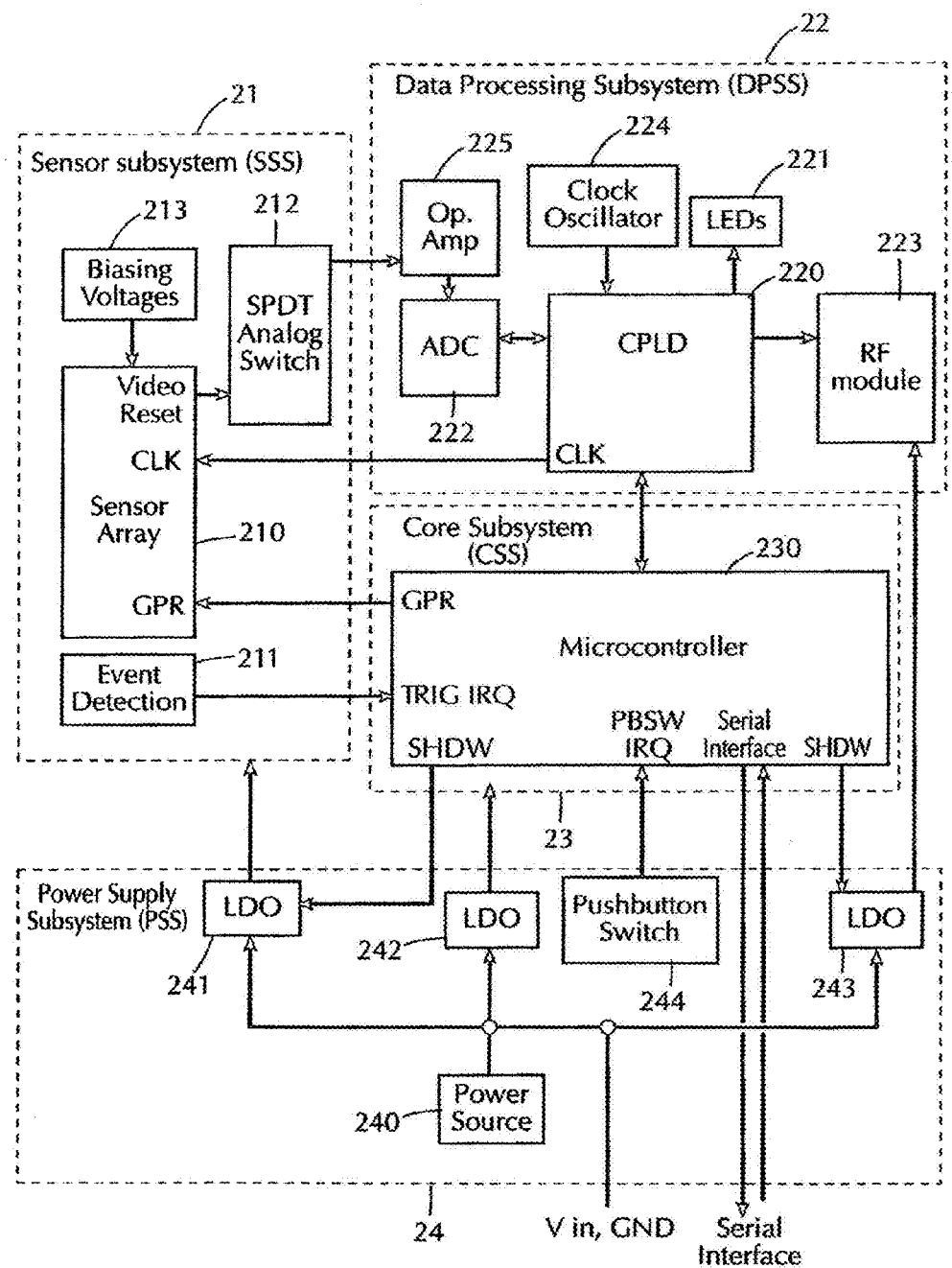
FIG. 10 is a schematic block diagram of a second intraoral x-ray system of U.S. Pat. No. 7,193,219.
Figure 11:
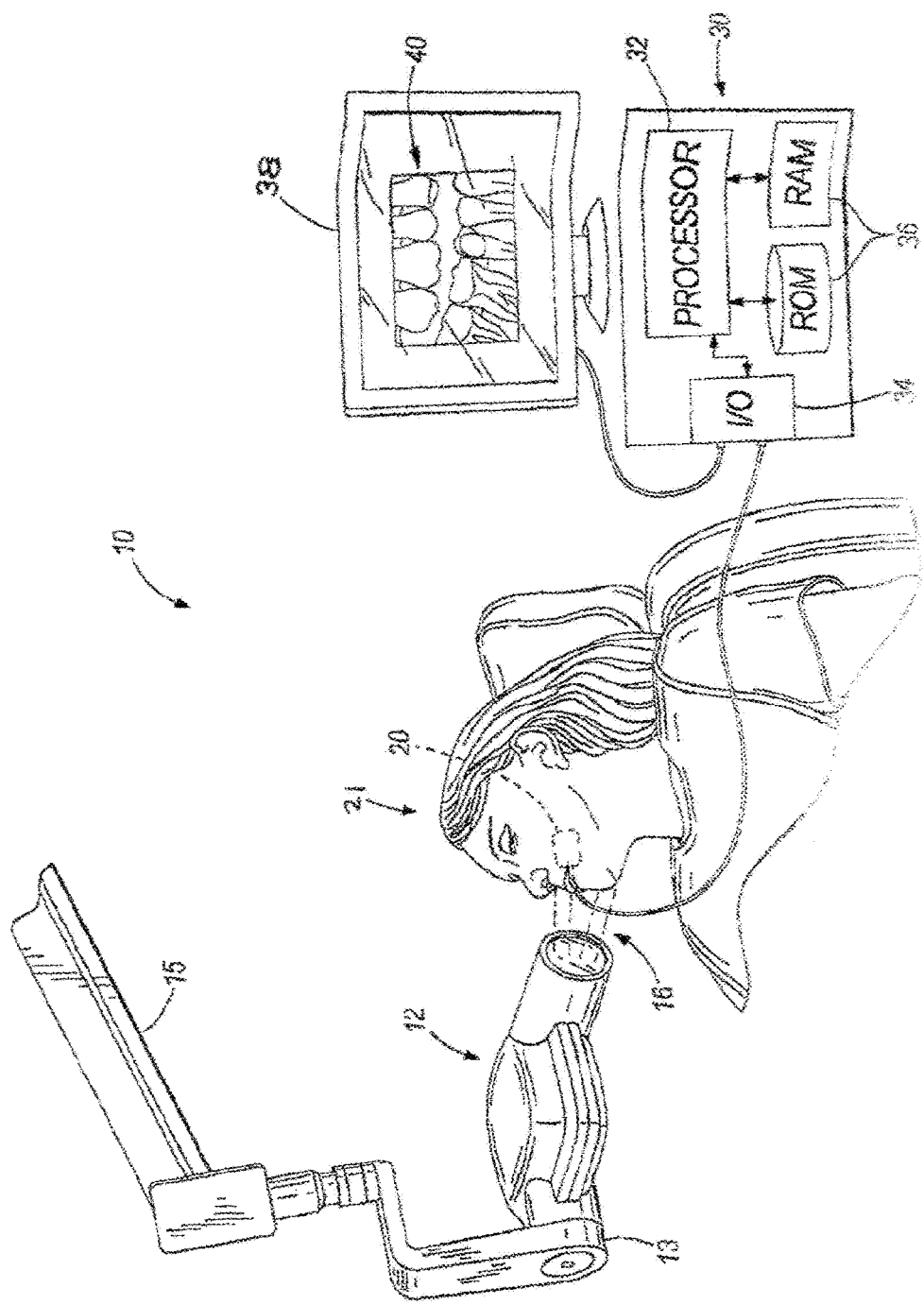
FIG. 11 is a perspective drawing of an intraoral x-ray system of U.S. Pat. No. 8,119,990.
Figure 12:
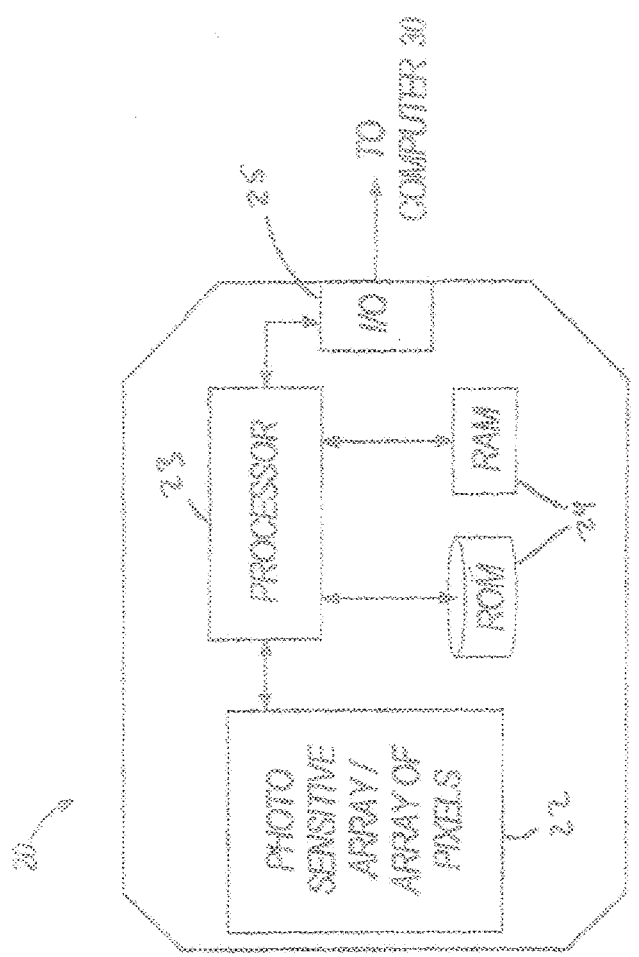
FIG. 12 is a schematic block diagram of the intraoral x-ray system of FIG. 11.

As computing methodologies of software development and deployment continue to advance, some of the most promising areas are cloud/wan/virtualized computing. In these environments, software is not typically installed like traditional software is installed locally on every Windows PC, or Mac that requires access. Rather, the software is installed on off-site/remote specialized powerful computer hardware and software that is managed by trained IT staff. Users interact with the software via a virtual private network (VPN) or via an internet connection. Typically all data is stored on the cloud/off-site. The concept is that this reduces complexity and costs for an organization and its users, and greatly increases access to the data because it is stored "on the cloud" and is accessible anywhere via simple internet connection. Virtualization promises to reduce local IT issues for users as they do not have to perform backups, and interchange of the data with other sources is easier.

Virtualization is basically the off-loading of as much of the tech, install, and backup and maintenance duties to someone who is specialized and who is usually physically not located at your facility. Virtualization and cloud has the effect of reducing client reliance on a specific type or manufacturer of PC hardware and the virtualized and/browser/cloud applications are more operating system agnostic. Because the client is effectively a remote screen viewer to the main server, the client hardware can be available on a much wider selection of devices including computers, phones, or other display devices. In addition, many cloud apps run in standardized browsers and can be same exact software on mac or pc as opposed to specific compiled versions for each type of device. As imaging systems continue to advance it is desired that sensors operate in the virtualized/cloud type of environments, and at the same time not lose any current functionality or speed.

Because in virtualized environments the "application software and/or storage" is actually operating on the "cloud" side (the internet side that is connected via slow internet upload speed) this dictates that the high bit depth grayscale image data from sensor must be uploaded (sent) to the cloud first, where the application software can process and/or store the high bit depth data and convert to a displayable image.

The virtualization/cloud deployment method of software/ storage operating on the server side, when combined with the physical operation of all current intraoral x-ray sensors outputting unprocessed high bit depth image data makes all current intraoral x-ray sensors nearly unusable in a true virtualized/cloud environment because the unprocessed high bit depth grayscale image data from sensor is just too large to upload quickly without affecting users workflow. The unprocessed high bit depth data is anywhere from 8-80+ times larger than the processed 8 bit lossy or lossless compressed grayscale image can be and all current generation sensors take far too long to transmit the data directly to the cloud/wan without processing high bit depth data and converting to low bit depth data first on a client PC.

Figure 13:
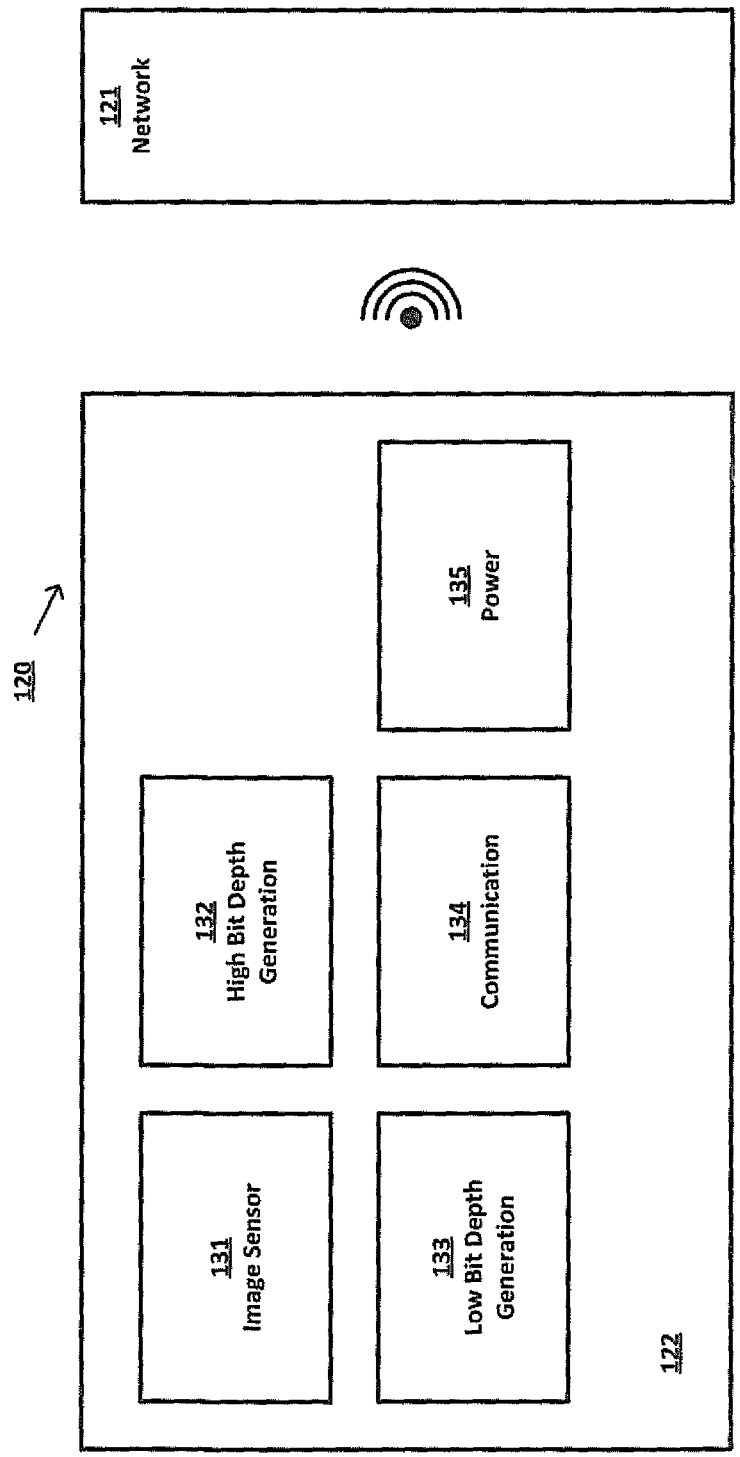
FIG. 13 is a schematic block diagram of the components of a first intraoral x-ray system which has a communication device which is wirelessly coupled to a network according to the first embodiment of the present invention.

Referring to FIG. 13 a first intraoral x-ray imaging device 120 produces intraoral images of a patient and is coupled to a network 121.

The first intraoral x-ray imaging device 120 includes intraoral housing 122 and an x-ray image sensor 131 which is disposed in the intraoral housing 122. The first intraoral x-ray imaging device 120 also includes a digital high-bit generator 132, a digital low-bit generator 133, a communication device 134 and a power source 135. The digital high-bit generator 132 is disposed inside the intraoral housing 122 and is coupled to the intraoral x-ray sensor 131 so that the digital high-bit generator 132 generates digital high bit depth grayscale sensor data. The digital low-bit generator 133 is disposed inside the intraoral housing 122 and is coupled to the digital high-bit generator 132 so that the digital low-bit generator 133 converts the digital high bit depth grayscale sensor data to digital low bit depth grayscale sensor data. The communication device 134 is disposed in the intraoral housing 122 and wirelessly couples the digital low-bit generator 133 to the network 121. The power source 135 is disposed in the intraoral housing 122 and provides power to the communication device 134.

Figure 14:
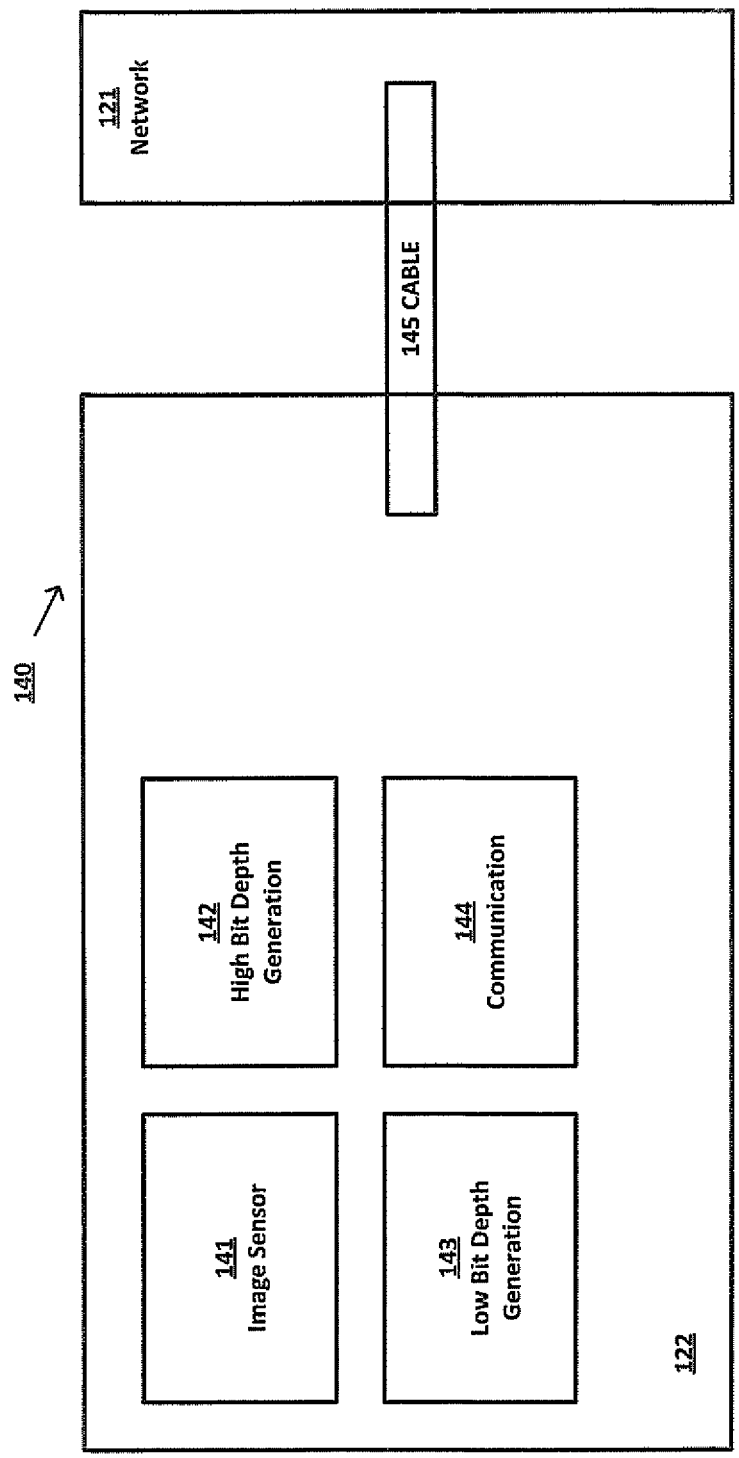
FIG. 14 is a schematic block diagram of the components of a second intraoral x-ray system which has a communication device which a cable couples to a network according to the second embodiment of the present invention.

Referring to FIG. 14 a second intraoral x-ray intraoral x-ray imaging device 140 produces intraoral images of a patient and is coupled to the network 121. The second intraoral x-ray imaging device 140 includes intraoral housing 122 and an x-ray image sensor 141 which is disposed in the intraoral housing 122. The second intraoral x-ray imaging device 140 also includes a digital high-bit generator 142, a digital low-bit generator 143 and a communication device 144 and a cable 145. The digital high-bit generator 142 is disposed inside the intraoral housing 122 and is coupled to the intraoral x-ray sensor 141 so that the digital high-bit generator 142 generates digital high bit depth grayscale sensor data. The digital low-bit generator 143 is disposed inside the intraoral housing 122 and is coupled to the digital high-bit generator 142 so that the digital low-bit generator 143 converts the digital high bit depth grayscale sensor data to digital low bit depth grayscale sensor data. The communication device 144 is disposed in the intraoral housing 122. The cable 145 couples the digital low-bit generator 143 to the network 121.

Figure 15:
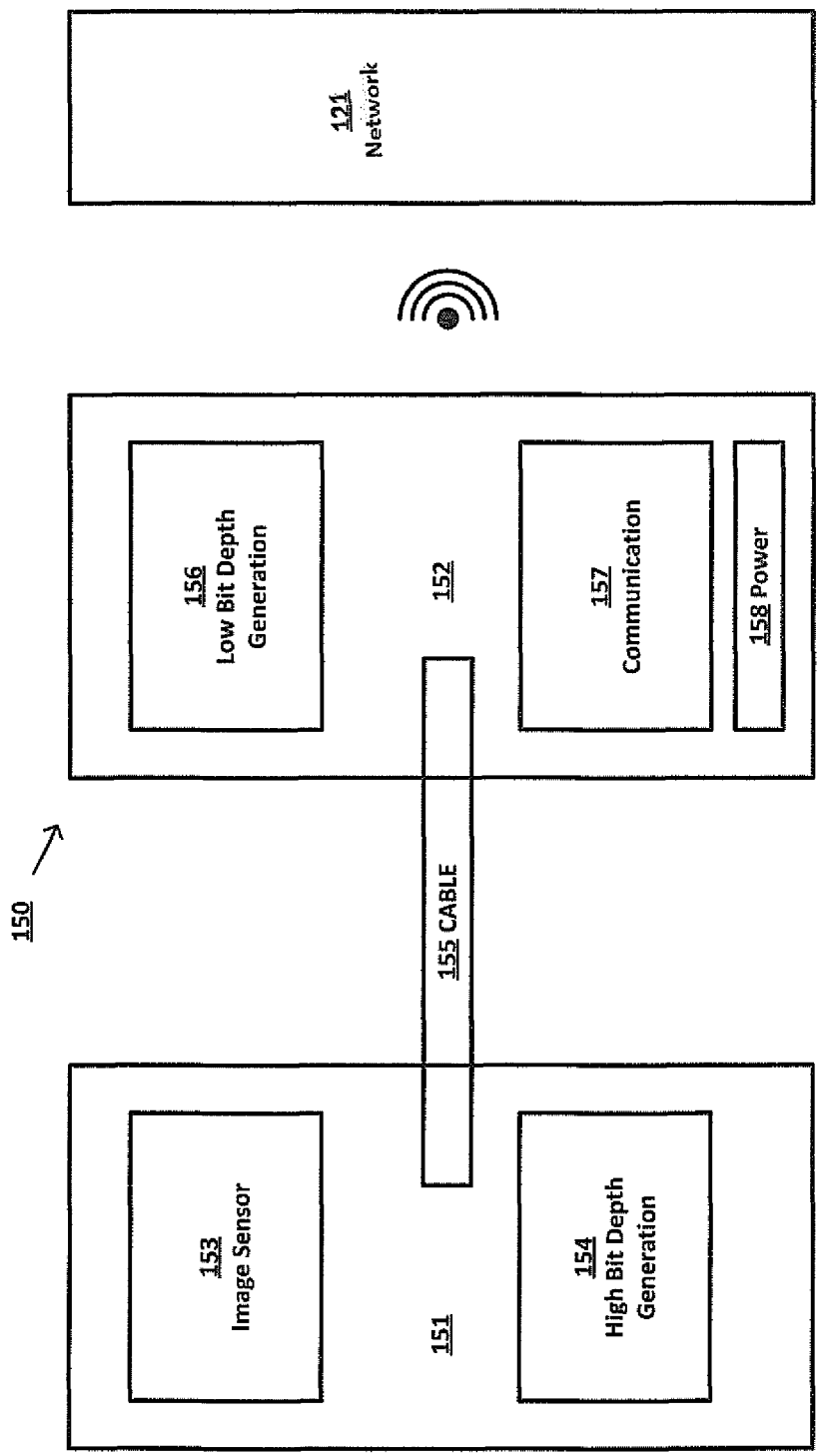
FIG. 15 is a schematic block diagram of the components of a third intraoral x-ray system which has a communication device which is wirelessly coupled to a network according to the third embodiment of the present invention.

Referring to FIG. 15 a third intraoral x-ray imaging device 150 produces intraoral images of a patient and is coupled to a network 121. The third intraoral x-ray imaging device 150 includes intraoral housing 151, tethered housing 152 and an x-ray image sensor 153 which is disposed in the intraoral housing 151. The third intraoral x-ray imaging device 150 also includes a digital high-bit generator 154 and a cable 155. The digital high-bit generator 154 is disposed inside the intraoral housing 151 and is coupled to the intraoral x-ray sensor 153 so that the digital high-bit generator 154 generates digital high bit depth grayscale sensor data. The third intraoral x-ray imaging device 150 further includes a digital low-bit generator 156, a communication device 157 and a power source 158. The digital low-bit generator 156 is disposed inside the tethered housing 152. The cable 155 couples the digital high-bit generator 154 to the digital low-bit generator 156 so that the digital low-bit generator 156 converts the digital high bit depth grayscale sensor data to digital low bit depth grayscale sensor data. The communication device 157 is disposed in the tethered housing 152 and wirelessly couples the digital low-bit generator 156 to the network 121. The power source 158 is disposed in the tethered housing 152 and provides power to the communication device 157.

Figure 16:
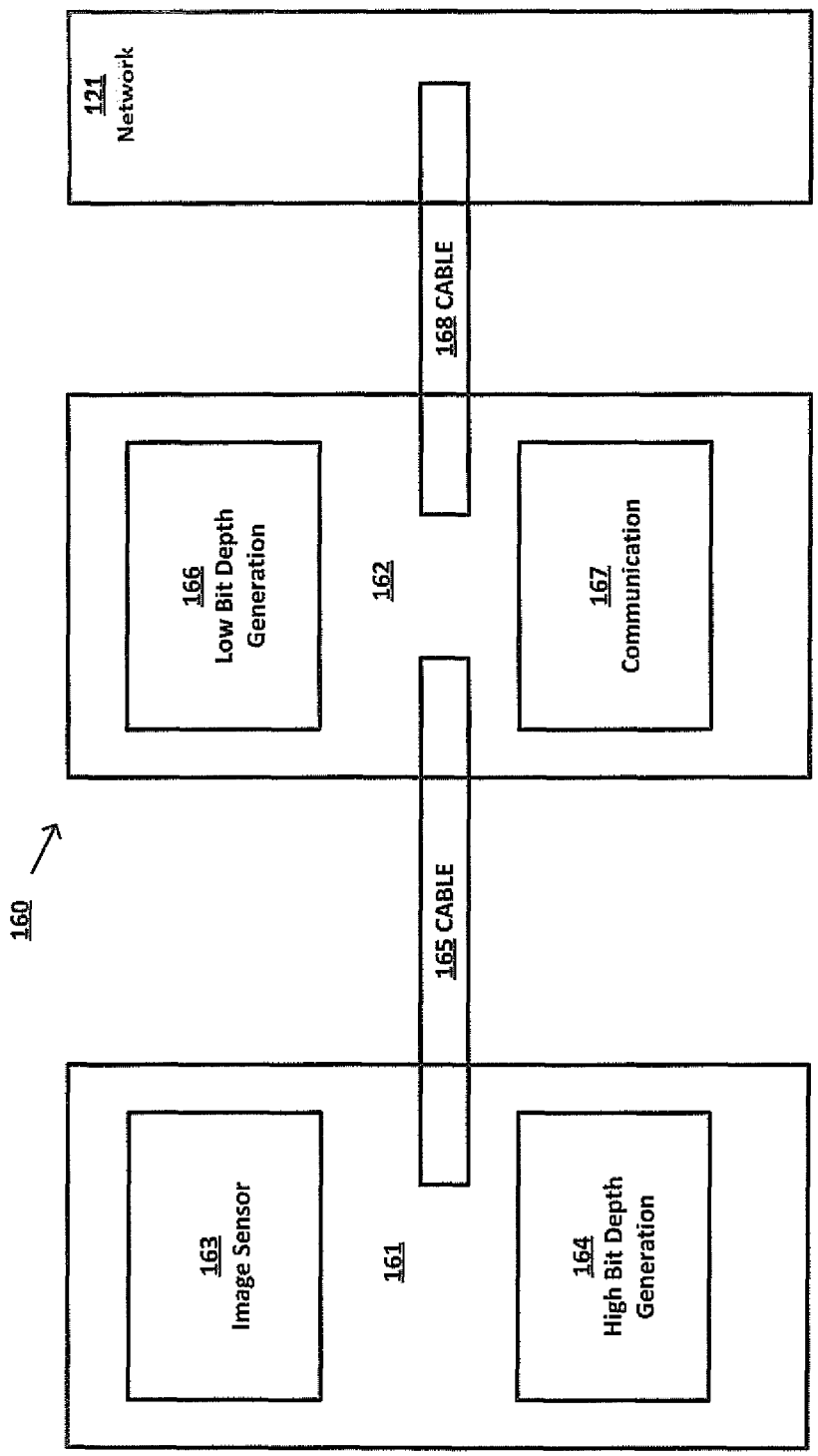
FIG. 16 is a schematic block diagram of the components of a fourth intraoral x-ray system which has a communication device which a cable couples to a network according to the fourth embodiment of the present invention.

Referring to FIG. 16 a fourth intraoral x-ray imaging device 160 produces intraoral images of a patient and is coupled to a network 121. The fourth intraoral x-ray imaging device 160 includes intraoral housing 161, tethered housing 162 and an x-ray image sensor 163 which is disposed in the intraoral housing 161. The fourth intraoral x-ray imaging device 160 also includes a digital high-bit generator 164 and a cable 165. The digital high-bit generator 164 is disposed inside the intraoral housing 161 and is coupled to the intraoral x-ray sensor 163 so that the digital high-bit generator 164 generates digital high bit depth grayscale sensor data. The fourth intraoral x-ray imaging device 160 further includes a digital low-bit generator 166, a communication device 167 and a cable 168. The digital low-bit generator 166 is disposed inside the tethered housing 162. The cable 165 couples the digital high-bit generator 164 to the digital low-bit generator 166 so that the digital low-bit generator 166 converts the digital high bit depth grayscale sensor data to digital low bit depth grayscale sensor data. The communication device 167 is disposed in the tethered housing 162. The cable 168 couples the digital low-bit generator 166 to the network 121.

Figure 17:
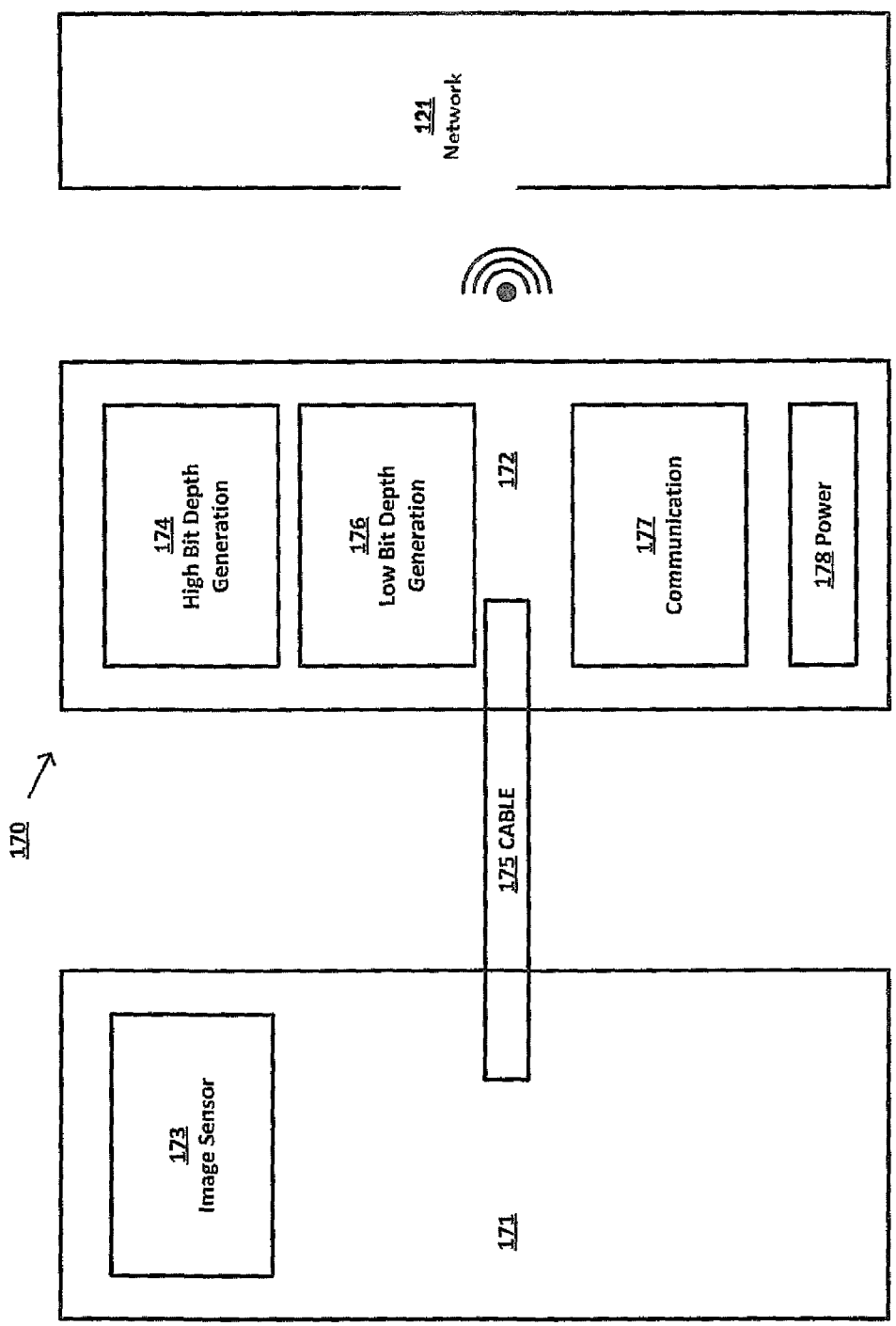
FIG. 17 is a schematic block diagram of the components of a fifth intraoral x-ray system which has a communication device which is wirelessly coupled to a network according to the fifth embodiment of the present invention.

Referring to FIG. 17 a fifth intraoral x-ray imaging device 170 produces intraoral images of a patient and is coupled to a network 121. The fifth intraoral x-ray imaging device 170 includes intraoral housing 171, tethered housing 172 and an x-ray image sensor 173 which is disposed in the intraoral housing 171. The fifth intraoral x-ray imaging device 170 also includes a digital high-bit generator 174 and a cable 175. The digital high-bit generator 174 is disposed inside the tethered housing 172. The cable 175 couples the intraoral x-ray sensor 173 to the digital high-bit generator 174 so that the digital high-bit generator 174 generates digital high bit depth grayscale sensor data. The fifth intraoral x-ray imaging device 170 further includes a digital low-bit generator 176, a communication device 177 and a power source 178. The digital low-bit generator 176 is disposed inside the tethered housing 172. The digital high-bit generator 174 is coupled to the digital low-bit generator 176 so that the digital low-bit generator 176 converts the digital high bit depth grayscale sensor data to digital low bit depth grayscale sensor data. The communication device 177 is disposed in the tethered housing 172 and wirelessly couples the digital low-bit generator 176 to the network 121. The power source 178 is disposed in the tethered housing 172 and provides power to the communication device 177.

Figure 18:
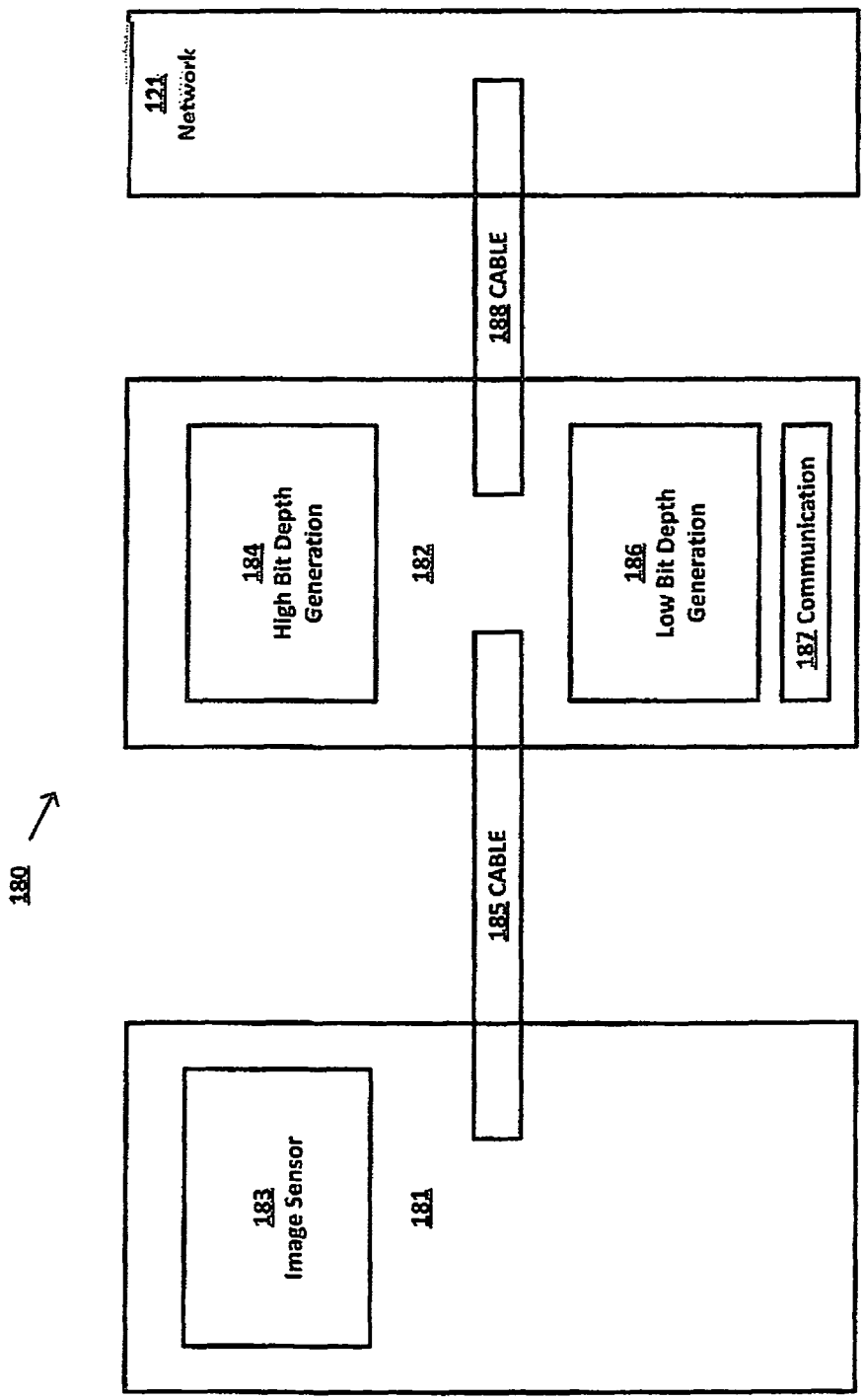
FIG. 18 is a schematic block diagram of the components of a sixth intraoral x-ray system which has a communication device which a cable couples to a network according to the sixth embodiment of the present invention.

Referring to FIG. 18 a sixth intraoral x-ray imaging device 180 produces intraoral images of a patient and is coupled to a network 121. The sixth intraoral x-ray imaging device 180 includes intraoral housing 181, tethered housing 182 and an x-ray image sensor 183 which is disposed in the intraoral housing 181. The sixth intraoral x-ray imaging device 180 also includes a digital high-bit generator 184 and a cable 185. The digital high-bit generator 184 is disposed inside the tethered housing 182. The cable couples the intraoral x-ray sensor 183 to the digital high-bit generator 184 so that the digital high-bit generator 184 generates digital high bit depth grayscale sensor data. The sixth intraoral x-ray imaging device 180 further includes a digital low-bit generator 186, a communication device 187 and a cable 188. The digital low-bit generator 186 is disposed inside the tethered housing 182. The digital high-bit generator 184 is coupled to the digital low-bit generator 186 so that the digital low-bit generator 186 converts the digital high bit depth grayscale sensor data to digital low bit depth grayscale sensor data. The communication device 187 is disposed in the tethered housing 182. The cable 188 couples the communication device 187 to the network 121.

Referring to FIG. 13 through FIG. 18 all of the above described intraoral x-ray imaging devices eliminate the above stated issues and allow an x-ray sensor to be used in cloud and virtualized environments in an optimized manner without sacrificing speed, image quality or workflow as compared to traditional local software and sensor deployments. To do this a sensor needed designed which has capability "in the sensor device" to perform all the required processing and to deliver to the sensors output, whether wired or wireless connection, a fully processed compressed or uncompressed displayable x-ray image. This processed image can then be immediately uploaded to the cloud or sent near real-time across wan. The sensor design requires no direct or indirect connection to the display device for the purpose of processing the image to a displayable image from the high bit depth data. This processing capability for our new sensor design may be located inside the sensor housing and/or in the cable attached to sensor and/or in the connector attached to the sensors cable. For use with existing sensors, the processing capability may be located in a small enclosure semi-permanently attached to end of the existing sensors cable. This allows upgrading existing sensors that do not contain the disclosed invention directly in the sensor or cable.

From the foregoing it can be seen that intraoral X-ray imaging devices with optimized image data output for communication with a network have been described. It should be noted that the sketches are not drawn to scale and that distances of and between the figures are not to be considered significant. Accordingly it is intended that the foregoing disclosure and showing made in the drawing shall be considered only as an illustration of the principle of the present invention.

What is claimed is:

1. An intraoral x-ray imaging device for producing and transferring intraoral images of a patient to a network, said intraoral x-ray imaging device comprising:
   a. an intraoral housing;
   b. an x-ray image sensor disposed in said intraoral housing;
   c. a digital high-bit generator which generates digital high bit depth grayscale sensor data disposed inside said intraoral housing; and
   d. a digital low-bit generator for converting said digital high bit depth grayscale sensor data to digital low bit depth grayscale sensor data disposed inside said intraoral housing.

2. An intraoral x-ray imaging device for producing and transferring intraoral images of a patient to a network according to claim 1 wherein said intraoral x-ray imaging device includes a power source disposed in said intraoral housing and a communication device which is coupled to said power source and which is wirelessly coupled to the network.

3. An intraoral x-ray imaging device for producing and transferring intraoral images of a patient to a network according to claim 1 wherein said intraoral x-ray imaging device includes a cable and a communication device which is coupled to said digital low-bit generator and which said cable couples to the network.

4. An intraoral x-ray imaging device for producing and transferring intraoral images of a patient to a network, said intraoral x-ray imaging device comprising:
   a. an intraoral housing;
   b. an x-ray image sensor disposed in said intraoral housing;
   c. a digital high-bit generator disposed inside said intraoral housing and coupled to said x-ray image sensor in order to generate digital high bit depth grayscale sensor data;
   e. a cable coupling said intraoral housing to said tethered housing; and
   f. a digital low-bit generator disposed inside tethered housing and coupled to said digital high-bit generator in order to convert said digital high bit depth grayscale sensor data to digital low bit depth grayscale sensor data.

5. An intraoral x-ray imaging device for producing and transferring intraoral images of a patient to a network according to claim 4 wherein said intraoral x-ray imaging device includes a power source disposed in said intraoral housing and a communication device which is coupled to said power source and which is wirelessly coupled to the network.

6. An intraoral x-ray imaging device for producing and transferring intraoral images of a patient to a network according to claim 4 wherein said intraoral x-ray imaging device includes a low-bit generator and which said cable couples to the network.

7. An intraoral x-ray imaging device for producing and transferring intraoral images of a patient to a network, said intraoral x-ray imaging device comprising:
   a. an intraoral housing;
   b. an x-ray image sensor disposed in said intraoral housing;
   c. a tethered housing
   d. a cable coupling said intraoral housing to said tethered housing;
   e. a digital high-bit generator disposed inside said tethered housing and coupled to said x-ray image sensor in order to generate digital high bit depth grayscale sensor data; and
   f. a digital low-bit generator disposed inside tethered housing and coupled to said digital high-bit generator in order to convert said grayscale sensor data.

8. An intraoral x-ray imaging device for producing and transferring intraoral images of a patient to a network according to claim 7 wherein said intraoral x-ray imaging device includes a power source disposed in said intraoral housing and a communication device which is coupled to said power source and which is wirelessly coupled to the network.

9. An intraoral x-ray imaging device for producing intraoral and transferring images of a patient to a network according to claim 7 wherein said intraoral x-ray imaging device includes a cable and a communication device which is coupled to said digital low-bit generator and which said cable couples to the network.

* * * * *